United States Patent
Oates et al.

(10) Patent No.: US 9,010,328 B2
(45) Date of Patent: *Apr. 21, 2015

(54) FLOW GENERATOR MESSAGE SYSTEM

(71) Applicant: ResMed Limited, Bella Vista, New South Wales (AU)

(72) Inventors: John David Oates, Sydney (AU); Mark David Buckley, Sydney (AU); Philip Rodney Kwok, Sydney (AU); Mark Alexander Abourizk, Sydney (AU); Thomas Evan Miller, Pittsford, NY (US); Simone Marie Jeha, Sydney (AU); Mark John Payne, Gosford (AU); Muditha Pradeep Dantanarayana, Sydney (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/845,413

(22) Filed: Mar. 18, 2013

(65) Prior Publication Data

US 2013/0206143 A1    Aug. 15, 2013

Related U.S. Application Data

(62) Division of application No. 12/067,234, filed as application No. PCT/AU2006/001506 on Oct. 13, 2006, now Pat. No. 8,424,514.

(60) Provisional application No. 60/726,178, filed on Oct. 14, 2005.

(51) Int. Cl.
*A62B 7/00*    (2006.01)
*A62B 9/00*    (2006.01)
(Continued)

(52) U.S. Cl.
CPC ........... *A61M 16/0066* (2013.01); *A61M 16/00* (2013.01); *A61M 16/0051* (2013.01);
(Continued)

(58) Field of Classification Search
USPC ............ 128/200.24, 202.22, 204.18, 204.23, 128/205.23; 340/309.7, 309.16, 539.12
See application file for complete search history.

(56) References Cited

U.S. PATENT DOCUMENTS 2,598,978 A    6/1952    Martin
(Continued)

FOREIGN PATENT DOCUMENTS

EP    1127583    7/2003
(Continued)

OTHER PUBLICATIONS

"Alarm clock". The Penguin English Dictionary. 2007. http://www.credoreference.com/entry/penguineng/alarm_clock (Sep. 30, 2013).*

(Continued)

*Primary Examiner* — Tan-Uyen (Jackie) T Ho
*Assistant Examiner* — Mark K Han
(74) *Attorney, Agent, or Firm* — Nixon & Vanderhye PC

(57) ABSTRACT

A flow generator for delivering breathable gas to a patient includes a processor coupled with operation sensors and a user interface. The processor is programmed to generate at least one of time-based or event-based messages relating to at least one of flow generator operation, flow generator service, flow generator use, patient health, peripheral devices and services, patient treatment, and reminders. Time-based messages are generated at predetermined time intervals based on either time of use or elapsed time. The event-based messages are generated based on signals from the operation sensors. The user interface is configured to deliver the messages to at least one of a display, a flow generator service provider, the patient and a physician. By this system, operation of the flow generator is facilitated and enhanced.

21 Claims, 2 Drawing Sheets

(51) Int. Cl.
  *F24F 5/00* (2006.01)
  *G08B 1/00* (2006.01)
  *A61M 16/00* (2006.01)
  *A61M 16/06* (2006.01)
  *A61M 16/08* (2006.01)

(52) U.S. Cl.
  CPC ....... *A61M16/0666* (2013.01); *A61M 16/0875* (2013.01); *A61M 2205/3561* (2013.01); *A61M 2205/3584* (2013.01); *A61M 2205/502* (2013.01); *A61M 2205/52* (2013.01)

(56) References Cited

U.S. PATENT DOCUMENTS

| | | | |
|---|---|---|---|
| 5,072,728 | A | 12/1991 | Pasternack |
| 5,490,502 | A | 2/1996 | Rapoport et al. |
| 5,503,146 | A | 4/1996 | Froehlich et al. |
| 5,844,862 | A | 12/1998 | Cocatre-Zilgien |
| 5,895,595 | A | 4/1999 | Haden |
| 6,119,686 | A | 9/2000 | Somerson et al. |
| 6,360,741 | B2 | 3/2002 | Truschel |
| 6,363,933 | B1 * | 4/2002 | Berthon-Jones ......... 128/204.23 |
| 6,425,395 | B1 | 7/2002 | Brewer et al. |
| 6,546,930 | B1 | 4/2003 | Emerson et al. |
| 6,678,215 | B1 | 1/2004 | Treyz et al. |
| 6,953,354 | B2 | 10/2005 | Edirisuriya et al. |
| 7,314,451 | B2 * | 1/2008 | Halperin et al. .............. 600/534 |
| 8,424,514 | B2 * | 4/2013 | Oates et al. .............. 128/200.24 |
| 2002/0022973 | A1 | 2/2002 | Sun et al. |
| 2002/0088464 | A1 | 7/2002 | Truschel |
| 2003/0076745 | A1 | 4/2003 | Chapman |
| 2003/0140924 | A1 * | 7/2003 | Aylsworth et al. ....... 128/204.26 |
| 2003/0187525 | A1 | 10/2003 | Mann et al. |
| 2003/0208465 | A1 * | 11/2003 | Yurko et al. ...................... 707/1 |
| 2003/0236450 | A1 | 12/2003 | Kocinski |
| 2004/0118403 | A1 | 6/2004 | O'Conner et al. |
| 2005/0076906 | A1 | 4/2005 | Johnson |
| 2005/0114182 | A1 | 5/2005 | Randolph et al. |
| 2009/0120437 | A1 | 5/2009 | Oates |

FOREIGN PATENT DOCUMENTS

| | | |
|---|---|---|
| EP | 1 449 558 | 8/2004 |
| WO | WO 96/28093 | 9/1996 |
| WO | 97/06843 | 2/1997 |
| WO | 01/00264 | 1/2001 |
| WO | 01/32069 | 5/2001 |
| WO | 01-91841 | 12/2001 |
| WO | 2004/049912 | 6/2004 |
| WO | 2005/011556 | 2/2005 |

OTHER PUBLICATIONS

Amended Notice of Opposition to Grant of Patent and Statement of Case issued Feb. 29, 2012 for corresponding New Zealand Application No. 567371.
International Search Report for PCT/AU2006/001506 mailed Jan. 30, 2007.
Written Opinion of the International Searching Authority for PCT/AU2006/001506, mailed Jan. 30, 2007.
International Preliminary Report on Patentability for PCT/AU2006/001506, mailed Jan. 30, 2007.
U.S. Appl. No. 10/533,940, filed Dec. 2006, Kenyon et al.
U.S. Appl. No. 60/656,880, filed Mar. 2005, Kwok.
U.S. Appl. No. 60/703,432, filed Jul. 2005, Kwok et al.
Amended Notice of Opposition to Grant a Patent, filed on Jan. 28, 2014 in New Zealand Application No. 591993.
Statement of Case, filed on Jan. 28, 2014 in New Zealand Application No. 591993.
Second Amended Notice of Opposition to Grant a Patent, filed on Jul. 18, 2014 in New Zealand Application No. 591993.
Amended Statement Of Case, filed on Jul. 18, 2014 in New Zealand Application No. 591993.
Second Amended Statement Of Case, filed on Sep. 29, 2014 in New Zealand Application No. 591993.
Statutory Declaration of Alex Young filed on Sep. 29, 2014 in New Zealand Application No. 591993.
Statutory Declaration of Andrew Baden Clark filed on Sep. 29, 2014 in New Zealand Application No. 591993.
Statutory Declaration of David Robin Whiting filed on Sep. 29, 2014 in New Zealand Application No. 591993.
Amended Counterstatement, filed on Aug. 21, 2014 in New Zealand Application No. 591993.
Statutory Declaration of Andrew Baden Clark, filed on Sep. 8, 2014 in New Zealand Application No. 600480.
Statutory Declaration of Haydn Llewellyn, filed on Sep. 8, 2014 in New Zealand Application No. 600480.
Second Amended Notice of Opposition to Grant a Patent, filed on Sep. 8, 2014 in New Zealand Application No. 600480.
Amended Statement Of Case, filed on Sep. 8, 2014 in New Zealand Application No. 600480.
Amended Counterstatement, filed on Oct. 15, 2014 in New Zealand Application No. 600480.
Third Amended Notice of Opposition to Grant of Patent, filed on Oct. 21, 2014 in New Zealand Application No. 591993.
Third Amended Statement of Case, filed on Oct. 21, 2014 in New Zealand Application No. 591993.

* cited by examiner

FLOW GENERATOR MESSAGE SYSTEM

CROSS-REFERENCES TO RELATED APPLICATIONS

This application is a division of application Ser. No. 12/067,234, filed Nov. 14, 2008 and now allowed; which is the U.S. national phase of International Application No. PCT/AU2006/001506 filed Oct. 13, 2006 which designated the U.S. and claims the benefit of U.S. Provisional Application No. 60/726,178, filed Oct. 14, 2005, each of which is incorporated herein by reference in its entirety.

STATEMENT REGARDING FEDERALLY SPONSORED RESEARCH OR DEVELOPMENT (Not Applicable)

BACKGROUND OF THE INVENTION

The present invention relates generally to flow generators for ventilatory assistance and, more particularly, to a flow generator that includes a message system for communicating messages relating to flow generator operation, flow generator service, flow generator use, patient health, peripheral devices and services, patient treatments, general reminders, and the like. Messages may be delivered to an onboard display or externally to a service provider, the patient, a physician, or the like.

Non-Invasive Positive Pressure Ventilation (NIPPV) is a form of treatment for breathing disorders which can involve providing a relatively higher pressure of air or other breathable gas to the entrance of a patient's airways via a patient interface (e.g., a mask) during the inspiratory phase of respiration, and providing a relatively lower pressure or atmospheric pressure in the patient mask during the expiratory phase of respiration. In other NIPPV modes the pressure can be made to vary in a complex manner throughout the respiratory cycle. For example, the pressure at the mask during inspiration or expiration can be varied through the period of treatment.

Continuous Positive Airway Pressure (CPAP) treatment is commonly used to treat breathing disorders including Obstructive Sleep Apnea (OSA). CPAP treatment continuously provides pressurized air or other breathable gas to the entrance of a patient's airways via a patient interface (e.g., a mask) at a pressure elevated above atmospheric pressure, typically in the range 3-20 cm $H_2O$. CPAP treatment can act as a pneumatic splint of a patient's upper airway.

CPAP treatment can be in a number of forms, including the maintenance of a constant treatment pressure level, alternating between two different constant levels in synchronism with the inspiratory and expiratory phases of respiration ("bi-level CPAP"), and having an automatically adjustable and/or a computer controlled level in accordance with a patient's therapeutic needs.

Breathable gas supply apparatus used in CPAP and NIPPV treatments broadly comprise a flow generator constituted by a continuous source of air or other breathable gas generally in the form of a blower driven by an electric motor. A pressurized supply of air or other breathable gas can also be used. The gas supply is connected to a conduit or tube, which is in turn connected to a patient interface (mask or nasal prong) which incorporates, or has in close proximity, a vent to atmosphere for exhausting exhaled gases, such as carbon dioxide.

BRIEF SUMMARY OF THE INVENTION

Patients using flow generators necessarily integrate the devices into their sleeping routine. The devices are used on a daily basis and greatly enhance the quality of life for patients requiring them. It would thus be desirable if the flow generators themselves could communicate with the users to maximize system effectiveness and therapy and facilitate use of the device in the patients' daily lives.

In this context, it is important that the device function and be operated properly, and it is desirable to enable the device to introspectively determine operating concerns or malfunctions. The present invention provides a flow generator that generates messages to facilitate use of the device. The messages may relate to aspects of the flow generator itself or to integrating the system into a patient's daily routine. The messages can be delivered over any suitable medium in any suitable manner, such as for example by written, graphical or audible messages. A related flow generator with a patient reminder system is disclosed in U.S. patent application Ser. No. 10/533,940, the contents of which are hereby incorporated by reference.

In an exemplary embodiment of the invention, a flow generator for delivering breathable gas to a patient includes a processor coupled with operation sensors and a user interface. The processor is programmed to generate one of time-based messages, event-based messages, or both time- and event-based messages relating to at least one of flow generator operation, flow generator service, flow generator use, patient health, peripheral devices and services, patient treatment, and general reminders. The time-based messages are generated at predetermined time intervals based on either time of use or elapsed time, and the event-based messages are generated based on signals from the operation sensors. The user interface is configured to deliver the messages to at least one of a display, a flow generator service provider, the patient and a physician.

The processor is preferably programmed to receive a reminder request input, wherein the time-based messages include reminders generated at a time specified in the reminder request input. The user interface may include a wireless communication system that communicates with at least one of a preset telephone number, a cellular phone, a pager, and a call center.

In one embodiment, the user interface is a network interface that delivers the messages via a global network such as the internet. In this context, the event-based messages may comprise messages relating to flow generator parts requiring replacement or repair. Moreover, the system may automatically order at least one of the parts requiring replacement or service for the repair. The network interface is preferably also configured to receive message content via the global network. The message content may comprise information relating to new products and peripherals cooperatively usable with the flow generator.

The flow generator may additionally include a memory that stores software executed by the processor and data relating to flow generator use and operation. The processor executes the software to generate the messages. In one embodiment, the memory is a data card.

The flow generator may still additionally include peripheral devices providing enhanced functionality. The peripheral devices communicate with the processor, wherein the time-based and event-based messages relate to use and operation of the peripheral devices.

The time-based messages may be customizable, for example, providing a personal reminder for the patient, a wake-up alarm or the like. The wake-up alarm may be an audio message or may be effected via the delivery of breathable gas to the patient. The messages may include advertisements generated at predetermined time intervals and/or upon the occurrence of at least one event relating to flow generator use and operation. The messages may relate to helpful user tips and may be interactive with the patient.

The event-based messages may be structured as notice levels relating to flow generator operation, where the notice levels are changed based on a use condition duration detected by the sensors. In one embodiment, the use condition is a leak, wherein a first notice level provides an indication that the leak has been detected, a second notice level provides another indication that the leak has been detected along with user tips to correct the leak, and a third notice level provides a communication notifying a service provider or physician of the leak.

In another exemplary embodiment of the invention, a CPAP apparatus includes a flow generator that generates a supply of pressurized air to be provided at an outlet; a patient interface engageable with a patient's face to provide a seal; and an air delivery conduit coupled between the flow generator and the patient interface to deliver the supply of pressurized air from the flow generator to the patient interface. The flow generator preferably includes a processor coupled with operation sensors and a user or communication interface.

In yet another exemplary embodiment of the invention, an identifier is provided for use with a flow generator that generates a supply of pressurized air to be provided at an outlet to a patient for treatment. The flow generator includes a processor coupled with operation sensors and a user interface, wherein the processor is programmed to generate time-based and/or event-based messages relating to at least one of flow generator operation, flow generator service, flow generator use, patient health, peripheral devices and services, patient treatment, and general reminders, wherein the time-based messages are generated at predetermined time intervals based on either time of use or elapsed time, and wherein the event-based messages are generated based on signals from the operation sensors. The identifier includes an identifying element providing an identifying feature unique to a specific peripheral component attachable to the flow generator. The processor discerns the specific peripheral component via the identifying feature. In this context, the time-based and event-based messages are generated based on use and operation of the specific peripheral component.

In still another exemplary embodiment of the invention, a method is provided for operating a flow generator that generates a supply of pressurized air to be provided at an outlet to a patient for treatment, the flow generator including a processor coupled with operation sensors and a user interface. The method includes the steps of generating either time-based or event-based messages relating to at least one of flow generator operation, flow generator service, flow generator use, patient health, peripheral devices and services, patient treatment, and general reminders, the time-based messages being generated at predetermined time intervals based on either time of use or elapsed time, and the event-based messages being generated based on signals from the operation sensors; and delivering the messages via the user interface to at least one of a display, a flow generator service provider, the patient and a physician.

BRIEF DESCRIPTION OF THE DRAWINGS

These and other aspects and advantages of the present invention will be described in detail with reference to the accompanying drawings, in which.

DETAILED DESCRIPTION OF PREFERRED EMBODIMENTS

Flow Generator

Figure 1:
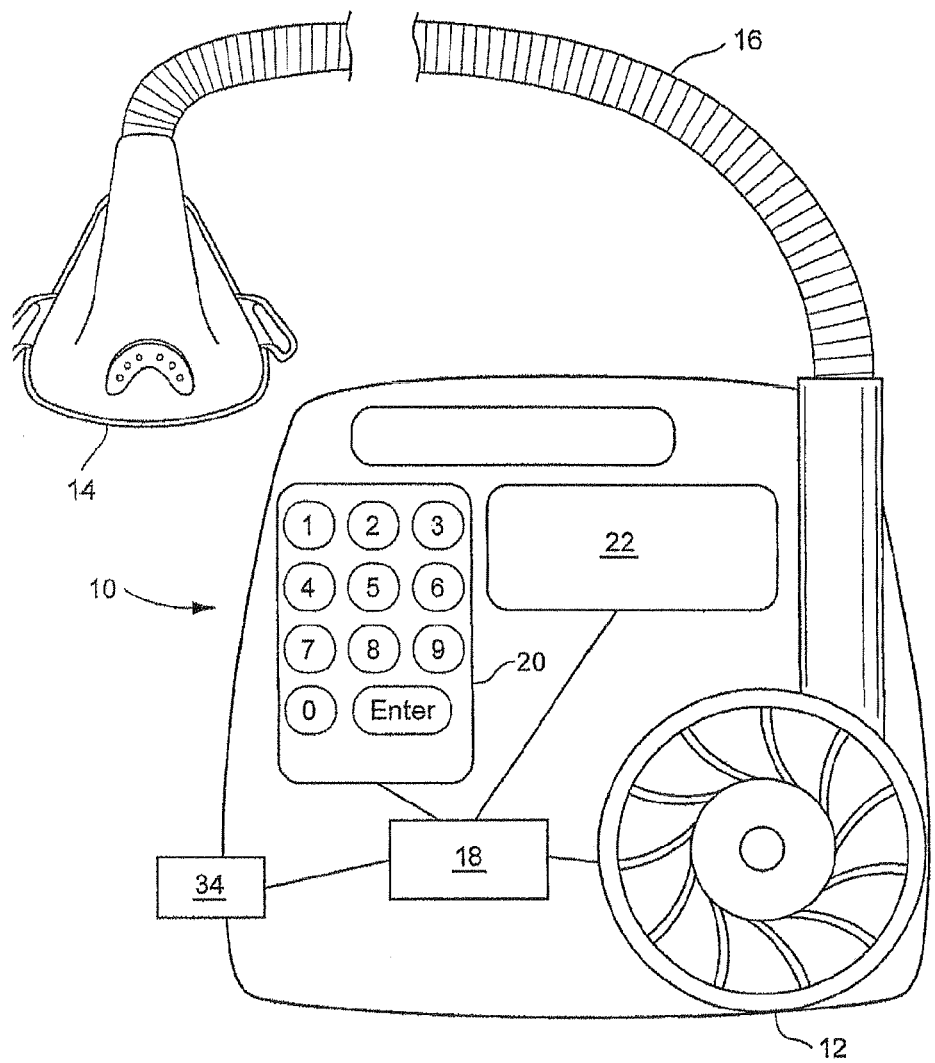
FIG. 1 is a perspective view of an exemplary flow generator.

The concepts of the present invention are suitable for any flow generator providing NIPPV and/or CPAP treatment, including but not limited to flow generators having motor controlled pressure regulation or valve pressure regulation. An exemplary flow generator structure will be described with reference to FIG. 1 for purposes of explanation.

A flow generator 10 includes a motor 12 that provides a supply of pressurized air for the administration of NIPPV and/or CPAP treatment. The pressurized air is delivered to a patient via a patient interface 14. An air delivery conduit 16 is coupled between the flow generator 10 and the patient interface 14. The patient interface 14 may have any suitable configuration as is known in the art, e.g., full-face mask, nasal mask, oro-nasal mask, mouth mask, nasal prongs, etc. Furthermore, the patient interface 14 also encompasses both vented and non-vented masks and dual limb mask systems. A processor 18 controls the operations of the flow generator. The flow generator is provided with a user interface unit or "communication system" 20 (which is generically intended to encompass both input and output systems of any suitable structure) to allow information input and a display unit 22 to display output information.

Communication System

Figure 2:
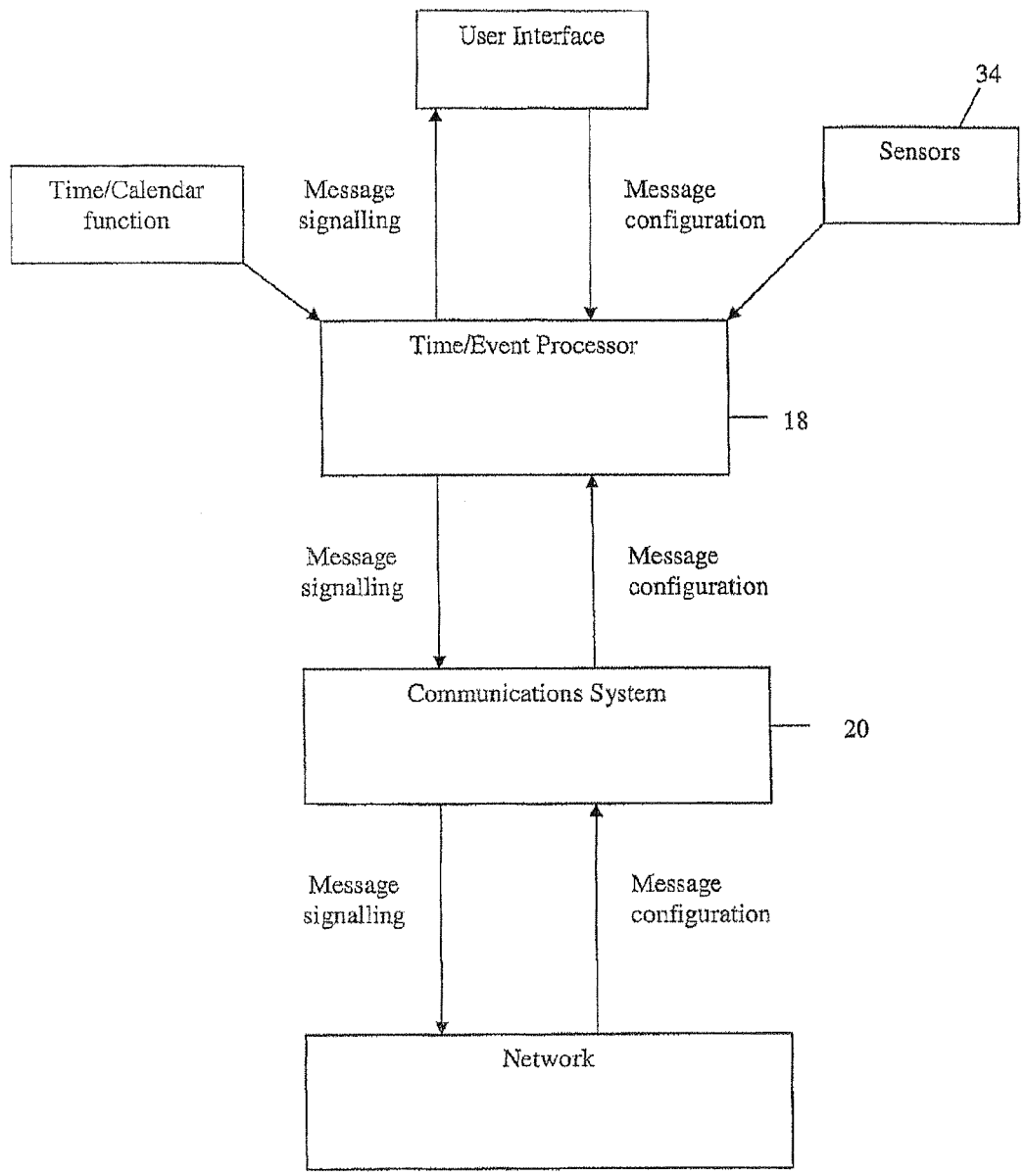
FIG. 2 is a schematic block diagram of the flow generator operating system and message/alarm functionality.

With reference to FIG. 2, the processor is coupled with the operation sensors (shown schematically at 34) and communication system 20. The processor is programmed to generate time-based or event-based messages relating to one or more of flow generator operation, flow generator service, flow generator use, patient health, peripheral devices and services, patient treatment, and general reminders or the like. The user interface or communications system 20 includes structure that effects delivery of the messages. Delivery of messages may be via the display unit 22 or via an external communication device such as a modem or wireless technology such as cellular telephony or via the internet through a network interface. With a remote communication system, the flow generator can also deliver messages to a physician, a flow generator service provider, the patient, or the like.

Time-Based Messages

The messages generated by the processor 18 may be time-based or event-based or both. Time-based messages are generated at predetermined time intervals based on either time of use or elapsed time. Examples of time-based messages include general reminders, where the processor is programmed to receive a reminder request input, and the messages comprise reminders generated at a time specified in the reminder request input. Examples of other time-based messages may include a notice that one or more parts should be replaced (after a certain period of use), a reminder concerning timing for a patient to schedule an appointment with their physician, a wake-up alarm, which may be an audible alarm or may be effected via the delivery of breathable gas to the patient such as via pulses of air or by pressure variations, and the like. The time-based messages may be customizable by the patient for use as a personal reminder. For example, the flow generator may be programmed to remind the patient to take their pills. Advertisements may also be generated at predetermined time intervals, possibly in relation to a time interval when a part such as the mask or filter should be replaced.

The time-based messages may also include helpful user tips to assist the user in maximizing flow generator functionality. A calendar and clock function enables use of the system to generate wake-up alarms as well as provide time-based messages based on either time of use or elapsed time. An example of a flow generator including a built in alarm clock is disclosed in U.S. Patent Application Ser. No. 60/703,432, filed Jul. 29, 2005, the contents of which are hereby incorporated by reference. Helpful tips and other use information can thus be provided to the patient based on the time of year. For example, the processor may be programmed such that it knows winter months are approaching (i.e., from the calendar) and can remind the patient to utilize their humidifier. In addition, the calendar and clock function can monitor user sleep cycle and awaken the user at non-REM sleep.

Event-Based Messages

Event-based messages are generated based on signals from the operation sensors 34 and are correlated to particular events or triggers detected by the processor 18 via the sensors 34. For example, the event-based messages may relate to flow generator parts requiring replacement or repair. The processor 18 can determine via the sensors 34 whether a particular part needs replacement or repair. For example, if a leak is detected in the mask, it may be that the mask needs to be replaced. The system may effect automatic ordering of one or more of the parts requiring replacement or generate a request for service or repair, which may be part of a user subscription. In concert with such a determination, the processor 18 may generate helpful tips to assist the user in properly positioning/wearing the mask. The processor 18 may generate advertisements as event-based messages, for example when parts need replacement or as new parts/products become available. In this context, the communication system 20 may be capable of receiving data as message content for example via the global network through the network interface. In this manner, the message content may include information relating to new products and peripherals cooperatively usable with the flow generator.

Peripheral Devices

The flow generator may additionally include peripheral devices providing enhanced functionality. In this context, the peripheral devices may be detected via an identifier including an identifying element providing an identifying feature unique to a specific peripheral component attachable to the flow generator. The processor 18 discerns the specific peripheral component via the identifying feature. This concept is described in detail in commonly-owned U.S. Patent Application Ser. No. 60/656,880, the contents of which are hereby incorporated by reference. In this manner, the messages generated by the processor 18 may relate to use and operation of the peripheral devices.

Notice Levels

In one embodiment, the event-based messages include notice levels relating to flow generator operation. The notice levels are changed based on a use condition duration detected by the sensors 34. For example, a use condition may be a leak at the mask. In this context, a first notice level may include an indication that the leak has been detected, a second notice level may include another indication that the leak has been detected along with user tips to correct the leak, and a third notice level may include a communication notifying a service provider or physician of the leak.

AHI Threshold

A patient's specific AHI (apnea-hyponea index) threshold may be entered into the device and monitored as an indicator of the effectiveness of the therapy. AHI is a measure of the number of apnea or hypopnea events that occur per hour of sleep, which is used to assess the severity of sleep disordered breathing (SDB). Commonly, an AHI of 5 or greater is considered to indicate mild OSA. Thus the AHI will vary amongst different patients, and consequently an AHI threshold will also vary between patients. The AHI threshold may be determined and entered by a clinician for an individual patient. The AHI or AHI threshold is an example of an event that may be monitored and reported on using the messaging system of the present invention. A change in the AHI index may be considered an indicator of how effective the therapy has been. For example a decrease in the AHI would indicate that the therapy was having a positive effect.

Monitoring System

A remote monitoring system is described in the U.S. patent application Ser. No. 10/934,540, the contents of which are hereby incorporated by reference. This system is not present in the flow generator but is a patient server comprising a database of rules governing payment of home care devices and the details for patients and devices. The system monitors when a patient is eligible to receive payment for further home care devices and may generate a reminder letter to send to the patient; thus reminding and encouraging patients to update their devices. The system may also be used to monitor drug prescription requirements. This type of reminder may also be included in the present application such that the reimbursement or payment details for a patient are entered into the device or may be selected from a list, and then in a similar manner the device will remind the patient when they are eligible to purchase further equipment.

Conclusion

The flow generator of the invention includes a message generating capability and communication structure that facilitate and enhance its use. The ability to communicate information to the user will reduce users' needs to contact the physician or product supplier with questions. The system can record events thereby reducing the burden and therefore labor and costs for processing insurance coverage. A calendar and clock function enables use of the system to generate wake-up alarms as well as provide time-based messages based on either time of use or elapsed time. Sensors enable the system to generate event-based messages. Of course, the examples described herein are exemplary, and those of ordinary skill in the art will appreciate that many variations of messages may be generated by the flow generator of the invention, and the invention is not necessarily meant to be limited to the described examples.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

The invention claimed is:

1. A flow generator for providing Continuous Positive Airway Pressure (CPAP) treatment to a patient with sleep apnea, the flow generator configured to provide a supply of pressurized breathable gas to a patient while the patient is sleeping, the flow generator comprising:
 a blower configured to supply pressurized breathable gas at a pressure between 3 and 20 cm $H_2O$ to pneumatically splint an airway of the patient while sleeping during CPAP treatment; and
 a processor coupled with operation sensors, a clock, and a user interface,
 wherein the processor is programmed to generate a time-based message, wherein the time-based message is generated at a predetermined time interval based on either time of use or elapsed time, and the flow generator is configured to deliver the time-based message to the patient by the adjustment of delivery of pressurized breathable gas to the patient during CPAP treatment,
 wherein the time-based message is a wake-up alarm.

2. A flow generator according to claim 1, wherein the time-based message is customizable.

3. A flow generator according to claim 1, wherein the time-based message comprises a personal reminder for the patient.

4. A flow generator according to claim 1, wherein the processor is programmed to generate at least one further time-based message, wherein the at least one further time-based message is generated at predetermined time intervals based on either time of use or elapsed time, and the user interface being configured to deliver the at least further one time-based message to at least one of a display, a flow generator service provider, the patient and a physician.

5. A flow generator according to claim 4, wherein the processor is programmed to receive a reminder request input, and wherein the at least one further time-based message comprises reminders generated at a time specified in the reminder request input.

6. A flow generator according to claim 5, wherein the reminder is related to the timing of a scheduled appointment with a physician.

7. A flow generator according to claim 5, wherein the reminder request input is programmed to remind the patient to take medication at a predetermined time.

8. A flow generator according to claim 4, wherein the user interface comprises a wireless communication system, the wireless communication system communicating with at least one of a preset telephone number, a cellular phone, a pager, and a call center.

9. A flow generator according to claim 4, wherein the user interface comprises a network interface, the network interface delivering the at least one further time-based message via a global network.

10. A flow generator according to claim 9, wherein the network interface is configured to receive message content via the global network.

11. A flow generator according to claim 10, wherein the message content comprises information relating to new products and peripherals cooperatively usable with the flow generator.

12. A flow generator according to claim 9, further comprising peripheral devices providing enhanced functionality, the peripheral devices communicating with the processor, wherein the at least one further time-based message relates to use and operation of the peripheral devices.

13. A flow generator according to claim 4, further comprising a memory that stores software executed by the processor and data relating to flow generator use and operation, the processor executing the software to generate the at least one further time-based message.

14. A flow generator according to claim 13, wherein the memory comprises a data card.

15. A flow generator according to claim 4, wherein the at least one further time-based message is customizable.

16. A flow generator according to claim 15, wherein the at least one further time-based message comprises a personal reminder for the patient.

17. A flow generator according to claim 15, wherein the at least one further time-based message comprises a wake-up alarm.

18. A flow generator according to claim 17, wherein the wake-up alarm is an audio message.

19. A flow generator according to claim 4, wherein the at least one further time-based message comprises advertisements.

20. The flow generator of claim 1, wherein the processor is further programmed to monitor a sleep cycle of the patient.

21. The flow generator of claim 20, wherein the processor is further programmed to cause delivery of the time-based message during a non-REM sleep stage of the patient in accordance with the monitored sleep cycle.

* * * * *